(12) United States Patent
Linder

(10) Patent No.: US 11,000,186 B2
(45) Date of Patent: May 11, 2021

(54) SYSTEMS AND METHODS FOR RETARDING MYOPIA PROGRESSION

(71) Applicant: Barry Jonathan Linder, Danville, CA (US)

(72) Inventor: Barry Jonathan Linder, Danville, CA (US)

(*) Notice: Subject to any disclaimer, the term of this patent is extended or adjusted under 35 U.S.C. 154(b) by 169 days.

(21) Appl. No.: 16/052,407

(22) Filed: Aug. 1, 2018

(65) Prior Publication Data

US 2019/0038123 A1 Feb. 7, 2019

Related U.S. Application Data

(60) Provisional application No. 62/540,441, filed on Aug. 2, 2017.

(51) Int. Cl.
| | | |
|---|---|---|
| *A61B 3/00* | (2006.01) | |
| *A61B 3/11* | (2006.01) | |
| *G02C 11/00* | (2006.01) | |
| *G02C 11/04* | (2006.01) | |

(52) U.S. Cl.
CPC ............ *A61B 3/0008* (2013.01); *A61B 3/112* (2013.01); *G02C 11/04* (2013.01); *G02C 11/10* (2013.01); *G02C 2202/24* (2013.01)

(58) Field of Classification Search
CPC ....... A61B 3/0008; A61B 3/112; G02C 11/10; G02C 2202/24
See application file for complete search history.

(56) References Cited

U.S. PATENT DOCUMENTS

2019/0282828 A1* 9/2019 Rucker ................ A61N 5/0613

FOREIGN PATENT DOCUMENTS

| CN | 203480152 U | * | 3/2014 | |
| WO | WO-2017113824 A1 | * | 7/2017 | ............. A47B 17/00 |

* cited by examiner

*Primary Examiner* — Jack Dinh
(74) *Attorney, Agent, or Firm* — Kang S. Lim

(57) ABSTRACT

Myopia is a clinically significant and growing problem around the world. A major cause is the increasing time spent indoors by children, for example, playing video games, studying, and watching television. Exposure to outdoor light is known to be protective, and prevents the onset and also delays the progression of myopia. Embodiments of the present invention provide simulated continuous outdoor light in either a closed or open feedback loop sufficient to retard myopia progression.

14 Claims, 5 Drawing Sheets

SYSTEMS AND METHODS FOR RETARDING MYOPIA PROGRESSION

BACKGROUND

The present invention relates to systems and methods for retarding the progression of myopia. More specifically, the invention pertains to use of simulated sunlight to illuminate the eyes to prevent myopia progression.

Myopia is often referred to as near or short sightedness. The incidence of myopia is increasing around the world, with the highest incidence in Asia. The condition is most often diagnosed in early school age children, and in most cases progresses during the subsequent years of school.

There is a growing body of evidence pointing to exposure to outdoor sunlight as a key factor in reducing the incidence of myopic progression in children. Numerous scientific studies have demonstrated the negative association between hours of lower light exposure levels and myopia progression. With increasing education levels, increased socioeconomic levels, and hours of study, the incidence of myopia has been increasing. Furthermore, the length of time spent indoors, e.g., in classrooms, is also increasing.

Currently, there are inadequate interventions that prevent or delay myopic progression. It is therefore apparent that an urgent need exists for effective medical intervention of myopia progression. These improved methods and devices accurately and safely simulate episodic levels of light exposure that children would receive from time outdoors, thereby substantially retarding the progression of myopia, especially in vulnerable K1-12 children.

SUMMARY

To achieve the foregoing and in accordance with the present invention, systems and methods for retarding myopia progression are provided. In particular the systems and methods for simulating sunlight to illuminate the eyes to retard myopia progression in school age children.

In one embodiment, a myopia progression retarder includes a light source, a sensor and a microprocessor. The light source provides illumination for simulating an outdoor lighting environment for a user. The sensor measures a pupillary response of the user thereby determining the presence and degree of a pupillary constriction. The microprocessor is operatively coupled to the light source and the sensor. The processor dynamically adjusts the provided illumination to solicit a target pupillary response from the user.

The myopia progression retarder can be integrated with an eyewear or a headgear. The retarder can also be incorporated into a computerized device such as a smart phone, tablet or a laptop.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "always," "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

Figure 1A:
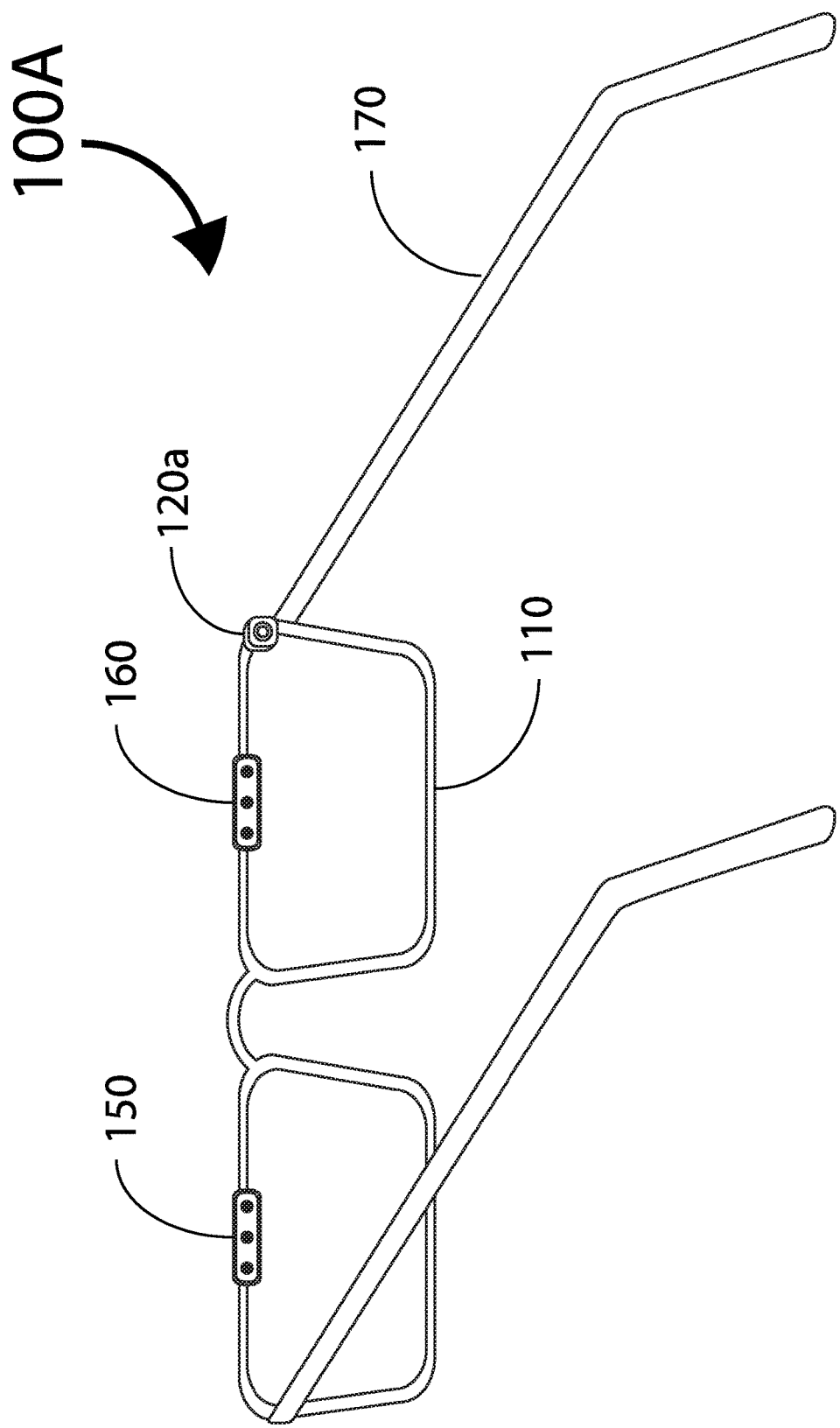
FIGS. 1A and 1B are perspective views of exemplary myopia progression retarders as implemented in eyewear, in accordance with some embodiments of the present invention.
Figure 1B:
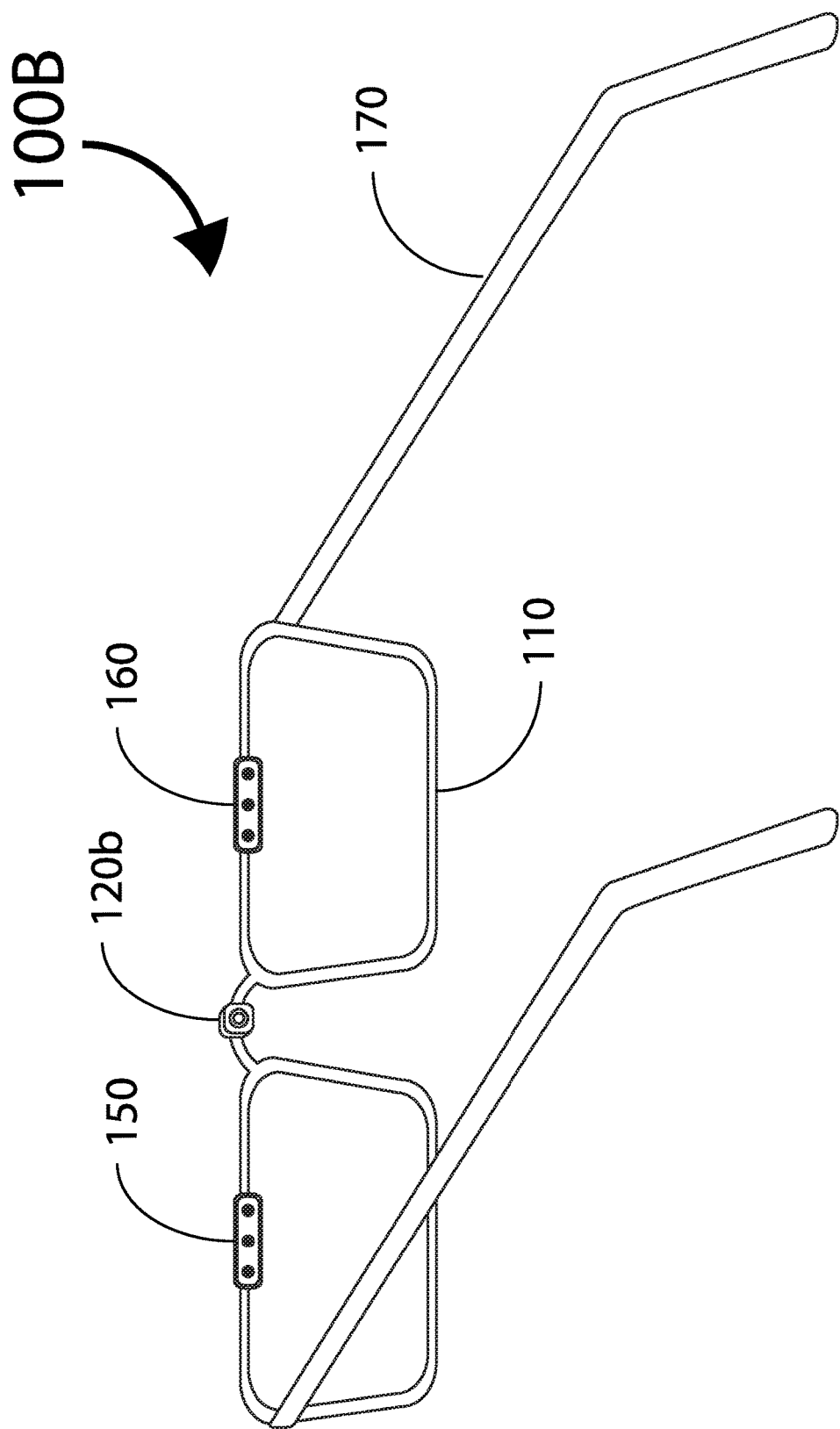

To facilitate discussion, FIGS. 1A and 1B illustrate exemplary embodiments of myopia progression retarders as implemented in eyewear, in accordance with the present invention.

In one embodiment, an eyewear 100A includes a frame 110, a video sensor 120a, and a pair of light sources 150, 160. A microprocessor/microcontroller and an optional transceiver (not shown) can be incorporated into the frame 110 and/or an earpiece 170.

A power source (not shown) can also be incorporated into the frame 110 and/or an earpiece 170. Suitable power sources include rechargeable and/or non-rechargeable batteries. Power can also be generated from head motion via accelerometers. Additional power sources include external wired AC/DC power. Optional supplemental power sources include solar cells. Myopia progression retarders may also be remotely charged via wireless focused-proximity charging and/or inductive charging.

Light sources 150, 160 are configured to simulate the intensity and frequency spectrum of outdoor light, especially sunlight, and can be generated by LEDs or any suitable light sources. Light sources 150, 160 may have adjustable parameters defined by the user and/or third part(ies), for example, a variety of light intensity levels including "Sunny", "direct exposure Sunny" and "in the shade Cloudy", as well as controllable weighting, bandpass, and filtering of wavelengths In some embodiments, eyeglass frames include integrated light source(s). The integrated light source can be unilateral or bilateral as illustrated by dual light sources 150, 160. The light source(s) can be a continuous Light Emitting Diode (LED), chosen with wavelengths that simulate the spectrum of natural outdoor light. The LED can have a variable luminance, controlled by the controlling microprocessor, with luminance of approaching 10,000 Lux to simulate the exposure expected outdoors on a typical sunny day.

Users and/or third part(ies) may also be able to control wavelength of illumination delivered to the user by eyewear 100A, such as illuminating with full spectrum of sunlight, variable wavelength(s), visible vs non-visible Bandwidth of chosen wavelength(s), and/or modulate wavelengths during exposure. Choices can also include displaying simultaneously one or more wavelength(s) and bandwidth(s).

In some embodiments, the angle of illumination of the light mounted on a set of frames relative to the entrance pupil of the user's eye can be adjustable. There can be several settings ranging from tangential illumination to nearly perpendicular to the eye's surface.

Video sensor 120a, e.g., a camera, can monitor physiologic pupillary response of the user to the light, thereby enabling the eyewear 100A to ensure adequate light exposure to obtain a target pupillary response. Recording use and compliance of the device is confirmed by active pupillary constriction (i.e. a user cannot simply turn on the light, but eyewear 100A is worn on a live person to obtain a pupillary response).

Video sensor 120a can be sensitive to visible "white" light and/or to other spectra such as infrared light. The purpose of sensor 120a is to monitor the pupillary reaction and size. Since the pupil response to light exposure is bilateral, only one eye's pupil need be monitored. Myopia progression retarders can be calibrated to illuminate the eye with a safe level of luminance that causes a pupillary constriction comparable to natural outdoor light levels. The retarders can work in a closed loop manner such that the controller device maintains the safe level of luminance to maintain the constricted pupil size. Alternatively, the light exposure can be delivered in an open loop manner to utilize a pre-set, non-variable level of light exposure. Further variations in illumination can be programmable, and include as examples alternating on-off-on patterns, as well as simulated illumination levels equal to a sunny day, cloudy day, or sunny day in the shade.

User usage data can be stored locally in eyewear 100A, in a remote server or a combination of both. Eyewear 100A may also be operatively coupled to an application running on a computer, smart phone and/or tablet, via a Bluetooth or WiFi wireless connection.

Usage data collected can include one or all of the following:
1. Duration of exposure
2. Pupillary response
3. Quantitative measure of eye movement
4. Time of day
5. Date
6. Illumination characteristics (wavelength, bandwidth, dynamics, intensity)
7. Head motion from embedded accelerometers
8. Light sensors measuring ambient light
9. Light sensors measuring level of delivered illumination In some embodiments, usage data can be uploaded to existing cloud database(s), such as adding clinical data to patient record, including refraction obtained from physician visits. Correlation to clinical condition can be performed (manually and/or automatically) and illumination recommendations are adjusted as needed to obtain improved clinical outcomes for specific user(s).

FIG. 1B illustrates a modified embodiment of an eyewear 100B which includes a frame 110, a video sensor 120b, and a pair of light sources 150, 160. In this embodiment, the video sensor 120b is located centrally with respect to frame 110.

Figure 2:
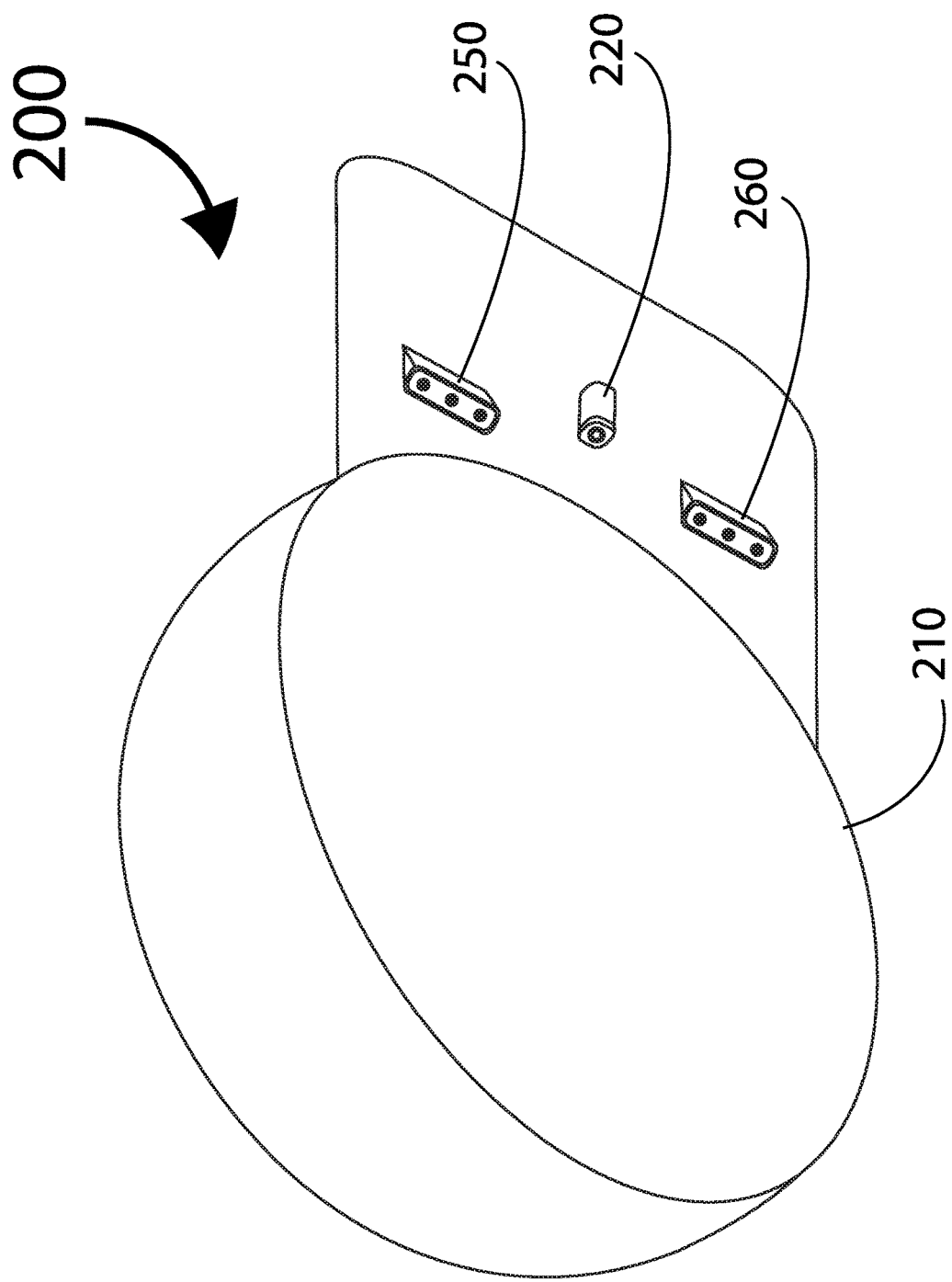
FIG. 2 is a perspective view of a myopia progression retarder as implemented in a headgear, in accordance with another embodiment of the present invention.

As illustrated in FIG. 2, in other embodiments, myopia progression retarders can be implemented in suitable headgear, e.g., a cap 200, having a video sensor 220 and light sources 250, 260. Other exemplary headgear suitable for incorporating myopia progression retarders include hats, visor, hoods and helmets.

It is contemplated that the location and number of light source(s) and camera(s) is not limited to the described embodiments. For example, a single camera can be located toward the center of the eyewear and capable of sensing pupil constriction of both eyes. Similarly, a single light source in located toward the middle of the headgear and provide illumination for both eyes.

For esthetic purposes, it is also possible for the light source(s) to be substantially concealed within the eyewear and the illumination (fiber) optically multiplexed, directed and eventually delivered at each eye through miniature lens. Such an arrangement can advantageously provide a more evenly distributed illumination around the frame and also reduces the weight on the nose piece thereby increasing user comfort and compliance.

In some embodiments, attachments may be added to eyewear or headgear to limit peripheral vision while reading indoors. The attachment can be made from an opaque material to allow ambient lighting to penetrate while blurring out objects otherwise within the user's peripheral field-of-vision.

Figure 3:
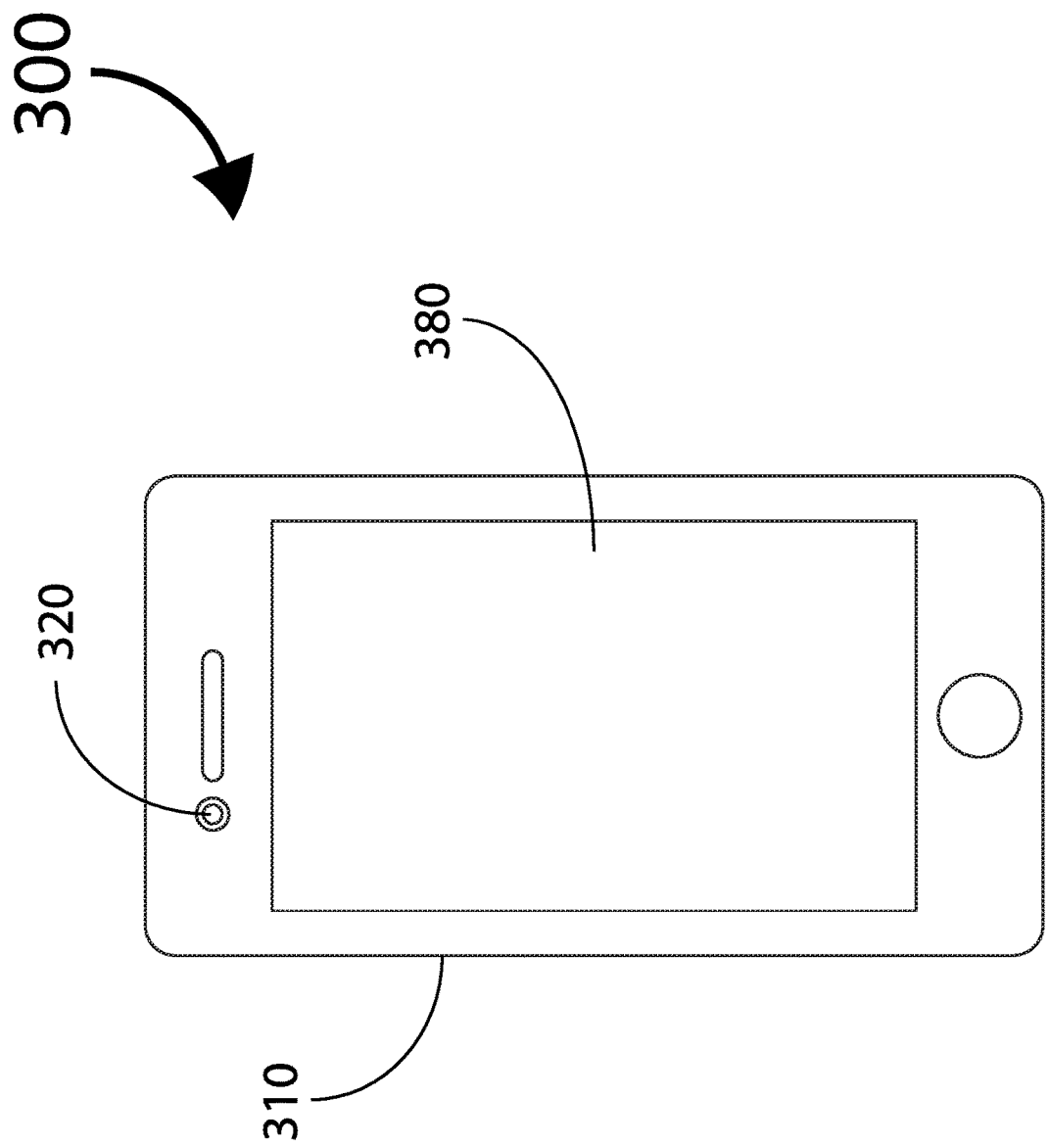
FIG. 3 is a perspective view of a myopia progression retarder as implemented in a smart device, in accordance with yet another embodiment of the present invention.

FIG. 3 depicts yet another embodiment of myopia progression retarder implemented in a computerized device, such as a smart device, a mobile phone, a tablet and a video monitor. In this example, smart phone 300 includes a user-facing camera 320 and a display screen 380 capable of outputting sufficient light intensity and spectrum to simulate sunlight. It is also possible to incorporate myopia progression retarders into Virtual Reality ("VR") or Augmented Reality ("AR") devices, such as VR googles and AR glasses, to provide the desired level of illumination to the user's eyes.

Figure 4:
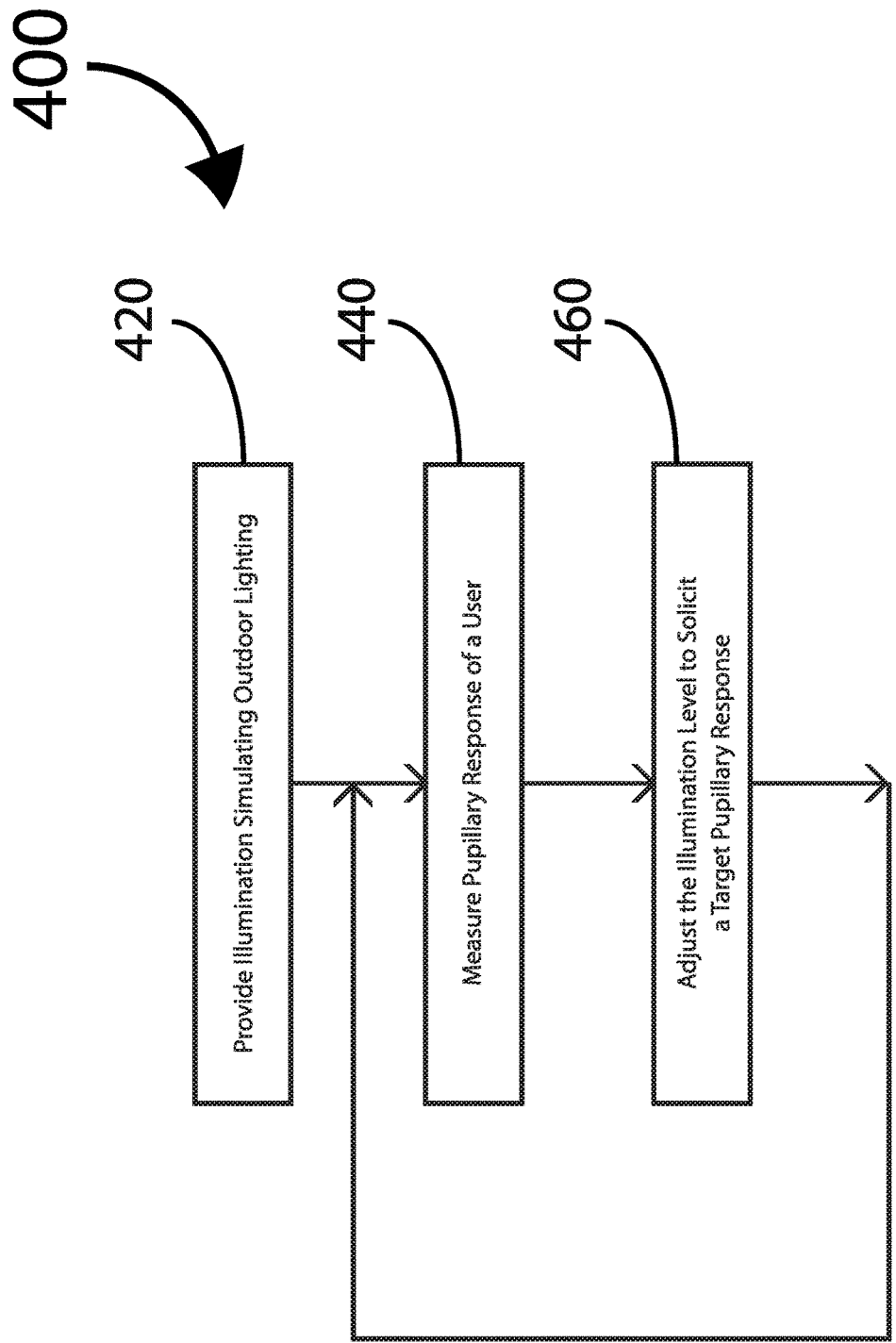
FIG. 4 is a flow diagram illustrating the operation of myopia progression retarders, in accordance with various embodiments of the present invention.

In sum, as illustrated by the flow diagram 400 of FIG. 4, a myopia progression retardation system provides illumination simulating outdoor lighting levels and/or spectrum for a user (step 420). The system measures pupillary response of at least one of the user's eyes (step 440). The system dynamically adjusts the level and/or spectrum of illumination to solicit a desired pupillary response, intended to delay the onset and/or retard the progression of myopia, by maintaining a target pupil constriction consistent with exposure to the outdoor lighting levels and/or spectrum (step 460).

Myopia progression retarders may be capable of communicating with each other and/or a central microprocessor controller in accordance with some embodiments of the present invention. The central controller of such a system can either be a dedicated controller device, or a smart portable device (such as an iPhone) with a software application. The controller can be configurable as a stand-alone device or operatively coupled to a central database via, for example, an internet cloud. Duration of light exposure, illumination level, and pupillary response can be recorded. In addition, a motion detector capable to measuring head movements for eyeglass frame mounted lighting can wirelessly send data to the central database.

Additional optional monitoring sensors can include location, time, integrated metadata including weather, ambient light, and camera to track eye movements, convergent and divergent binocular eye movements, eye targeting movements, and pupillary responses. Real-time automated monitoring of the central data base using artificial intelligence and data mining can also be implemented, and reports routinely generated, or alerts generated if it appears that the lighting system is either not used as recommended, or has been removed from the eyewear or headwear.

Many additional variations and modifications are possible. For example, the light source(s) and camera can be independent components in a kit with universal adaptors to fit each element on any eyeglass frame. Yet another variation of the myopia progression retarder includes the light source without a camera, and the controller works in an open loop manner with pre-set continuous illumination levels.

Alternatively, instead of a video sensor, a solar cell measures the ambient light at the user's location. The myopia progression retarder then computes the amount of supplemental illumination needed to simulate an equivalent outdoor daytime lighting environment.

It is also possible for an external light that simulates light level and spectrum of the outdoor light exposure. This configuration allows the camera and light source to be mounted on stands in a convenient location to the user. A camera can still be utilized to measure pupillary response to ensure sufficient light levels to simulate outdoor exposure. For example, in a classroom setting, a group myopia progression retardation system can include desk-mounted cameras and individualized overhead illumination settings.

Other variants of myopia progression retarders include incorporation of miniature peripheral LED components into a contact lens with peripheral reflective elements to direct light centrally toward the pupil.

While this invention has been described in terms of several embodiments, there are alterations, modifications, permutations, and substitute equivalents, which fall within the scope of this invention. It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A myopia progression retarding system comprising:
    a light source configured to provide illumination for simulating an outdoor lighting environment for a user;
    a sensor configured to measure a pupillary response of the user thereby determining a pupillary constriction, and
    a processor operatively coupled to the light source and the sensor, wherein the processor is configured to dynamically adjust the illumination provided by the light source to solicit a target pupillary response from the user consistent with exposure to the outdoor lighting environment.

2. The system of claim 1 wherein an intensity of the illumination is approximately 10,000 Lux.

3. The system of claim 1 wherein a spectrum of the illumination is equivalent to natural sunlight.

4. The system of claim 1 wherein the system is integrated into an eyewear.

5. The system of claim 1 wherein the system is integrated into a headgear.

6. The system of claim 1 wherein the system is integrated into a computerized device.

7. The system of claim 6 wherein the computerized device is one of a smart phone, a tablet and a laptop.

8. The system of claim 1 wherein the system is integrated into a Virtual Reality ("VR") device.

9. The system of claim 1 wherein the system is integrated into an Augmented Reality ("AR") device.

10. A method for retarding myopia progression, the method comprising:
    providing illumination to simulate an outdoor lighting environment for a user;
    measuring a pupillary response of the user to determine a pupillary constriction; and
    dynamically adjusting the provided illumination to solicit a target pupillary response from the user consistent with exposure to the outdoor lighting environment.

11. The method of claim 10 wherein an intensity of the illumination is approximately 10,000 Lux.

12. The method of claim 10 wherein a spectrum of the illumination is equivalent to natural sunlight.

13. The method of claim 10 wherein the illumination is provided by an eyewear.

14. The method of claim 10 wherein the illumination is provided by a computerized device.

* * * * *